(12) United States Patent
Warburton

(10) Patent No.: US 7,491,547 B1
(45) Date of Patent: Feb. 17, 2009

(54) FILTER FOR GAS SENSOR

(76) Inventor: Piers Richard Warburton, 1619 Ridge Rd., Moon Township, PA (US) 15108

( * ) Notice: Subject to any disclaimer, the term of this patent is extended or adjusted under 35 U.S.C. 154(b) by 722 days.

(21) Appl. No.: 10/979,038

(22) Filed: Nov. 2, 2004

Related U.S. Application Data

(60) Provisional application No. 60/517,880, filed on Nov. 7, 2003.

(51) Int. Cl.
*G01N 33/00* (2006.01)
(52) U.S. Cl. .......... 436/127; 55/524; 73/31.07; 95/285; 436/142; 436/177
(58) Field of Classification Search .......... 422/58, 422/83–86, 101; 436/127, 142, 177; 204/431, 204/432; 73/23.2, 31.7; 55/522, 524, 525; 95/273, 285
See application file for complete search history.

(56) References Cited

U.S. PATENT DOCUMENTS

| | | | | |
|---|---|---|---|---|
| 4,272,480 A | * | 6/1981 | Stull et al. | 422/58 |
| 4,327,575 A | * | 5/1982 | Locker | 73/31.02 |
| 4,597,942 A | * | 7/1986 | Meathrel | 422/57 |
| 4,612,026 A | * | 9/1986 | Pollara et al. | 96/117.5 |
| 4,633,704 A | * | 1/1987 | Tantram et al. | 73/31.05 |
| 5,744,697 A | * | 4/1998 | Martell et al. | 73/31.06 |
| 5,865,973 A | * | 2/1999 | Kiesele et al. | 204/415 |
| 6,170,318 B1 | * | 1/2001 | Lewis | 73/23.34 |
| 6,284,545 B1 | * | 9/2001 | Warburton et al. | 436/124 |
| 2003/0086835 A1 | * | 5/2003 | Suzawa et al. | 422/180 |

OTHER PUBLICATIONS

A.R. Reiche "Safe Use of Ethylene Oxide in the Hospital Environment", in "Essentials of Modern Hospital Safety" Ed. W. Charney, J. Schirmer, Lewis Publishers, Chelsea MI (1991) Background information on ethylene oxide use as a sterilant gas.

* cited by examiner

*Primary Examiner*—Joseph W Drodge

(57) ABSTRACT

A filter that allows specific detection of ethylene oxide by a non-specific electrochemical gas sensor through the removal of potential interferent gases, such as alcohols, and carbon monoxide. The filter contains an oxidizing agent that will oxidize the interferent gas but not ethylene oxide or alternatively a polymeric material that allows selective hydrogen bonds to the interferent gas but not ethylene oxide. This filter is intended for use with ambient air gas monitors, such as those employed to enhance work-place safety.

18 Claims, 2 Drawing Sheets

FILTER FOR GAS SENSOR

PRIORITY

This application claims the benefit of priority of provisional application 60/517,880, filed Nov. 7, 2003.

FIELD OF THE INVENTION

The field of this invention is a chemical filter to increase the specificity of a gas monitor

BACKGROUND OF THE INVENTION

Ethylene oxide (ETO) is widely used in the chemical industry as a feed stock chemical, and is also commonly used as a sterilant gas, in for example, hospitals and medical equipment suppliers. ETO is one of the most efficient sterilant gases available, especially for those articles that cannot be sterilized by exposure to high temperatures. (A. R. Reiche "Safe Use of Ethylene Oxide in the Hospital Environment", in "Essentials of Modem Hospital Safety" Ed. W. Charney, J. Schirmer, Lewis Publishers, Chelsea Mich. (1991)). Ethylene oxide is a highly toxic gas, and the OSHA permissible workplace exposure limit for ethylene oxide is only 1.0 ppm averaged over an eight-hour shift (29 CFR 1910.1047). Thus, it is important to have adequate protection of personnel who are using ethylene oxide and it is common practice to use gas detection monitors to warn of potential leaks or other exposure to ethylene oxide. In a typical hospital application, gas detection monitors will be located near the sterilizers and in storage areas where ethylene oxide gas is kept. In addition, ethylene oxide monitors may also be deployed near or within abators used to destroy any ethylene oxide remaining in the waste gas stream from the sterilizers.

Currently, the two most frequently used technologies for continuously monitoring ETO in the workplace are electrochemical gas sensors and gas chromatography (GC). While GC has very good sensitivity and reproducibility, it has several drawbacks. Specifically, the GC method is inherently a spot check method since a sample is drawn into the instrument and then analyzed. For a typical monitoring application, at least four sampling points need to be analyzed, drawing gas from various locations. These points are sampled sequentially, not simultaneously, and with cycle times between samples on the order of two to three minutes there is every possibility that a leak of ETO could potentially not be detected for up to twelve minutes. In addition, GC based instruments tend to be large and bulky, require a supply of carrier gas and are usually expensive. Despite these limitations, GC based instruments are still widely used for monitoring ethylene oxide.

The other major technology for detecting ethylene oxide employs electrochemical sensors. The ethylene oxide enters the sensor, usually by diffusion from the ambient air, but sample draw equipment may also be used to deliver the ethylene oxide to the sensor. Once the ethylene oxide is in the sensor, it is oxidized at the working electrode and the resulting electric current is measured to provide a quantitative indication of the ethylene oxide concentration. Instruments using ETO electrochemical sensors are available from companies such as Chemdaq Inc., Pittsburgh Pa.

While instruments employing electrochemical sensors provide continuous monitoring, alarm upon high exposure to ETO, and have the sensitivity to detect 0.1 ppm ETO, they also possess drawbacks. In particular, the electrochemical sensors that are used to detect ETO respond to a wide range of easily oxidizable compounds, such as alcohols and carbon monoxide. Alcohols in particular are a problem because of their ubiquitous use in hospital environments. This cross sensitivity can result in false alarms and a loss of user confidence in the instruments.

Alcohols are easily oxidized, primary alcohols such as ethanol ($CH_3CH_2OH$) are oxidized to the corresponding carboxylic acid (e.g. ethanol to acetic acid) and secondary alcohols are oxidized to the ketone (e.g. isopropanol to acetone). If a monitor is exposed to either ethylene oxide or an alcohol vapor the monitor will give a response and at higher concentrations the monitor will give an alarm. However, the user does not know whether the monitor is responding to ethylene oxide and so should take remedial action or if the monitor is responding to the alcohol in which case it is safe to ignore the alarm. Consequently cross sensitivity of alcohols is one of the major drawbacks of using electrochemical sensors for ethylene oxide.

Alcohol is typically found in many medical environments, since it is a standard method for sterilizing equipment, work surfaces and skin. Alcohol is a common additive in many products, for example the hand sterilizers that are commonly used in medical facilities contain a gel comprised of about 80% w/w ethanol. For the purposes of this disclosure, the term alcohol corresponds to any small aliphatic alcohol, and especially ethanol and isopropanol.

Alcohol vapor is of particular concern in those locations where both alcohol and ethylene oxide may be found. For example a sterilization room in a hospital may use an alcohol based cleaner/sterilizer to sanitize the work surface (counter tops etc.) near the sterilizers. Since most alcohols are volatile (B.P. ethanol=76° C.), alcohol vapors are often found in the same vicinity as ethylene oxide monitors.

Several gas sensors incorporate chemical filters in an attempt to reduce the cross sensitivity to interferent gases. Filters are placed in the gas path such that all the gas that reaches the sensor must pass through the filter. The filter is designed to remove the interferent gas but not the target gas. However chemical filters cannot be used for all types of gas sensors being limited by the available chemistry to differentiate between the target and interferent gases. The use of chemical filters within sensors is well known in the prior art; for example, Tantram and Chan in U.S. Pat. No. 4,633,704 describe the use of a soda lime filter to prevent hydrogen sulfide from giving a response on a carbon monoxide sensor; and Warburton and Sawtelle described a filter based on silver salts also to remove hydrogen sulfide in U.S. Pat. No. 6,284,545. There are many filter materials that will remove alcohols from a gas stream, for example, charcoal filters are commonly used to protect carbon monoxide gas sensors from interferent gases including alcohols, as is illustrated by Kiesele et al in U.S. Pat. No. 5,865,973 and by Martell et al in U.S. Pat. No. 5,744,697, but no filters are known that remove easily oxidizable gases but also allow ethylene oxide to pass through substantially unimpeded.

One common type of filter employs an oxidizing agent, such as potassium permanganate. Commercially available potassium permanganate impregnated filter media for air filtration are available from companies such a Purafil Inc., Doraville, Ga. Potassium permanganate is a strong oxidizing agent, and oxidizes any alcohol which comes into contact with the filter medium, thus preventing it from entering the sensor.

The drawback is that ethylene oxide was also found to be oxidized by potassium permanganate and so the filter will prevent the ethylene oxide from getting into the sensor as well. Thus this type of filter is only suitable for relatively few types of gas sensors, such as those for carbon monoxide. Similarly ethylene oxide readily absorbs on common adsorbents such as activated charcoal and so these filters also cannot be used with ethylene oxide sensors. No chemical filter is available in the prior art that will allow ethylene oxide to pass through, but which will remove interferences such as alcohols and carbon monoxide.

Ethylene oxide is considered a highly reactive gas (hence its great toxicity), whereas alcohols are typically much less reactive, and considerably less toxic, as illustrated by the number of ethanol containing beverages currently available. In addition to being more reactive than ethanol, ethylene oxide reacts with acids and bases via hydrolysis to produce ethylene glycol ($HO-CH_2CH_2-OH$), which is chemically and physically similar to ethanol ($CH_3CH_2-OH$) making chemical differentiation more difficult.

At present the electrochemical sensors offer the best all round technology for detecting ethylene oxide, despite their cross sensitivity drawbacks. Clearly, there is a need for a filter that is suitable for use with an electrochemical gas sensor which will prevent interference from alcohols and other easily oxidizable volatile chemicals but which will still allow ethylene oxide to reach the gas sensor.

SUMMARY OF THE INVENTION

It is therefore an object of the invention to provide a filter for use with ethylene oxide sensors for removal of alcohols without adversely affecting the response of the sensor to ethylene oxide.

It is a further object of this invention to provide a filter for use with ethylene oxide sensors for removal of carbon monoxide without adversely affecting the response of the sensor to ethylene oxide.

It is a further object of this invention to provide a filter for use with ethylene oxide sensors for removal of easily oxidizable volatile compounds without adversely affecting the response of the sensor to ethylene oxide.

DETAILED DESCRIPTION OF THE INVENTION

Figure 1:
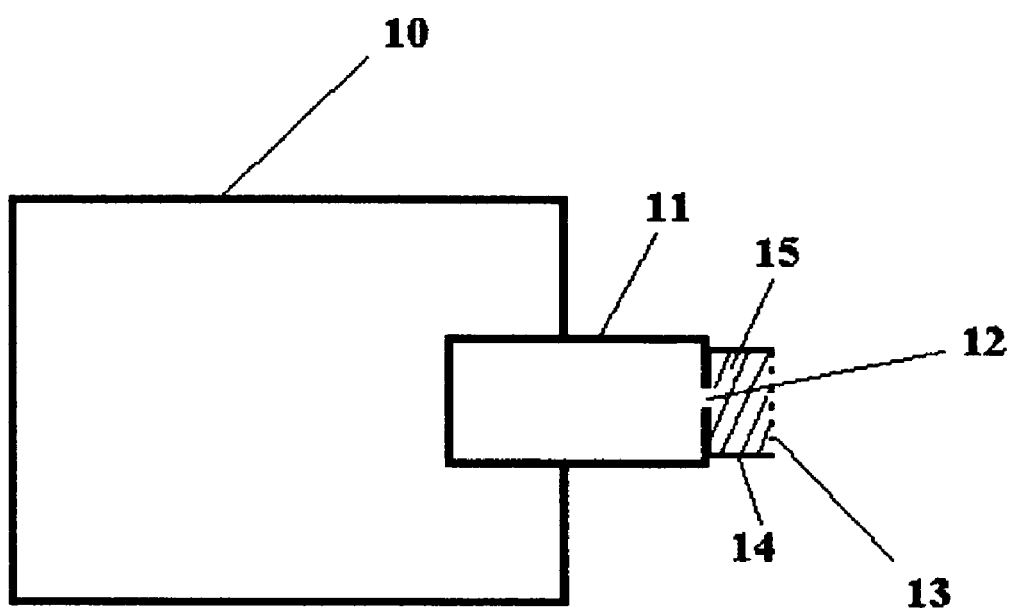
FIG. 1 is a cross-sectional diagram of a gas detection apparatus showing a filter operating in a diffusion mode.

The filter medium used to prepare the filter of the present invention is selected from among those chemical compounds that will react with alcohol present as an impurity in a gaseous medium and thus remove the alcohol from the gaseous medium without additional contamination. The reaction should occur at a rate, given the dimensions of the filter and the amount of alcohol in the gas, such that substantially no alcohol passes through the filter to reach the ethylene oxide sensor. Furthermore, the reagent and the filter substrate should be substantially non-reactive with ethylene oxide to allow ethylene oxide to pass through the filter essentially unchanged in concentration.

The theories outlined herein are presented for information purposes and represent the inventor's best understanding of the operation of the filter but the disclosure of the theories presented is not intended to provide any limitation on the scope of the invention. There are two classes of compounds that have been found to remove alcohol vapor from the air and yet allow ethylene oxide to pass through relatively unhindered. Despite being flammable and even explosive under some conditions, ethylene oxide has some resistance to mildly oxidation conditions. The first class of chemicals for use in the filter is oxidizing agents.

Strong oxidizing agents will oxidize alcohols, but a careful balance is required in the selection of the oxidizing agent for the filter. If the compound is insufficiently oxidizing then it will not react with and remove the alcohols. If the compound is too strongly oxidizing, then the compound will also oxidize and remove the ethylene oxide. For example cerium (IV) compounds are strong oxidizing agents and were found to remove both ethylene oxide and alcohol vapors. Silver nitrate is a weaker oxidizing agent and it was found not to react with either the alcohol or the ethylene oxide.

Preferred compounds include high valent compounds of manganese, lead, silver, cadmium, mercury, tin, with suitable counter ions including but not limited to oxides, hydroxides, nitrates, and the most preferred compounds include silver (II) oxide and lead (IV) oxide and manganese (IV) oxide.

In addition to removal of alcohols, filters employing oxidizing agents are expected to be able to remove any easily oxidizable volatile compounds (EOVCs) that can be oxidized by the filter material. Examples of EOVCs include carbon monoxide, hydrogen sulfide, sulfur dioxide, nitric oxide as well as organics such as aldehydes.

Another method for removing alcohols and yet allowing ethylene oxide to reach the sensor is to provide a material that selectively absorbs the alcohol. Both ethylene oxide and alcohols such as ethanol can hydrogen bond with other polar compounds such as water. However, whereas alcohols have an ionizable hydrogen and so can provide the hydrogen for the hydrogen bonding, which is called herein active hydrogen bonding, ethylene oxide can only hydrogen bond with a compound that can donate a hydrogen to it, called herein passive hydrogen bonding. Therefore, a filter material that is comprised of a very polar compound that is capable of passive hydrogen bonding only will be able to hydrogen bond to the alcohol but not to the ethylene oxide. Thus ethylene oxide will be allowed to pass through a filter made of such a material and the alcohol will be retained. Compounds that have been found to be suitable include polar passive hydrogen bonding polymeric compounds such as but not limited to polyvinylpyrrolidone, polyethylene oxide, poly(4-vinylpyridine), polystyrene cross linked tertiary amine. Other compounds that have been found to selectively absorb ethylene oxide include polystyrene sulfonic acid.

In particular polymers including basic functional groups, have been found to preferentially absorb alcohols over ethylene oxide, such basic functional groups include amines, aromatic and cyclic nitrogen containing compounds such as aniline, pyridine, pyrrole, and imidazole. In addition to polymers, solid materials e.g. silica, alumina and refractory oxides, with these compounds or polymers containing these functional groups attached or absorbed on the surface or within the pore structure of the supporting material can also be used. Obviously there are many other materials that can be designed so as to provide this differential absorption or adsorption of alcohols over ethylene oxide and their selection with the invention information herein disclosed is within the skill of those experienced in the chemical arts.

Other materials that are able to passively hydrogen bond may also be used within the scope of this invention and similarly their selection in light of the description provided herein is within the skill of those experienced in the chemical arts.

These filters can be used with any type of gas sensor in which the intention is to detect ethylene oxide in the potential presence of alcohols and similar interferent compounds, such as aldehydes or other gases or vapors that these filters can remove. The filters may be placed on the outside of the sensor or they may be incorporated within the sensor at manufacture. The key positional requirement is that the filter must be in the gas path, thus any gas which is going to enter the sensor must pass through the filter.

Similarly, the filter materials described above can be used in other applications where it is desirable to allow the passage of ethylene oxide into a device but not alcohols, for example an activated charcoal sampling tube or other chemical monitor.

If the filter is being used as an in-line filter, such that the gas is flowing through the filter material, then the filter needs to be constructed of a suitable material which presents a high surface area to the gas, but which does not present too much back pressure. If the back pressure is too high, then there is potential for inefficiency and strain on the pump, and increased risk of leaks around the filter or tears forming in the filter material. The physical strength requirements of an in-line filter are greater than those wherein the gas passes through by diffusion, since an in-line filter must be able to withstand a pressure drop.

If the filter material is placed in front of the sensor or in the sensor, such that the gas passes through the filter by natural diffusion, then the filter medium needs to be selected so that the filter does not present an excessive diffusion barrier to the gas. Even a porous filter will present a diffusion barrier to the gases reaching the sensor, and the greater the diffusion barrier, the greater the reduction in the sensitivity of the sensor. Furthermore, a larger diffusion barrier due to the filter will result in a longer response time from the sensor.

The amount of gas which is required to flow through the filter will depend on the instrument design, but the size of the filter and the capacity of the filter will have to be selected to meet the expected demand for interferent gas removal. Thus, a filter designed for an application where a sensor may occasionally be exposed to, for example, 1-2 ppm alcohol may differ from an application where there is a constant 10 ppm background alcohol. Similarly, a filter which is located behind a diffusion barrier within a sensor will require less capacity (or will last longer) than a similar filter in front of the sensor. If insufficient reagent is deposited on the filter support, then the filter will fail to remove all of the alcohol, or it will have a limited capacity to remove alcohol. In a preferred embodiment, the filter chemicals are either as a coarse powder, granules or as deposited on a porous support, such as alumina, silica or a glass fiber disk.

A typical application of the present invention is shown in FIG. 1. A gas detection instrument 10 for ethylene oxide incorporates a sensor 11 that operates in diffusion mode. Both the sensor 11 and the instrument 10 are conventional. The sensor 11 may for example be an electrochemical sensor. Gas would normally enter the sensor as part of the detection process via aperture 12 by natural diffusion. The sensor 11 would detect the ethylene oxide within the gas and provide a suitable electronic signal to the instrument 10. In order to prevent interferent gases from reaching the sensor 11 and causing false signals, a filter material 15 is placed inside a suitable filter enclosure 14. This filter enclosure attached over the aperture 12 of the sensor 11 so that the gas to be detected must pass into the filter enclosure 14 through a opening 13, pass through the filter 15 before it can enter the sensor 11 via the aperture 12. The filter enclosure 14 is typically constructed of plastic (e.g. polyethylene, ABS etc.) or other materials that provide a means to keep the filter material 15 in the gas path in front of the sensor aperture 12 and provides means for the gas to enter the filter enclosure via a suitable opening 13 comprised of, for example, sintered plastic. The design of the filter enclosure is simple and conventional for anyone experienced in the art of mechanical design and construction.

Figure 2:
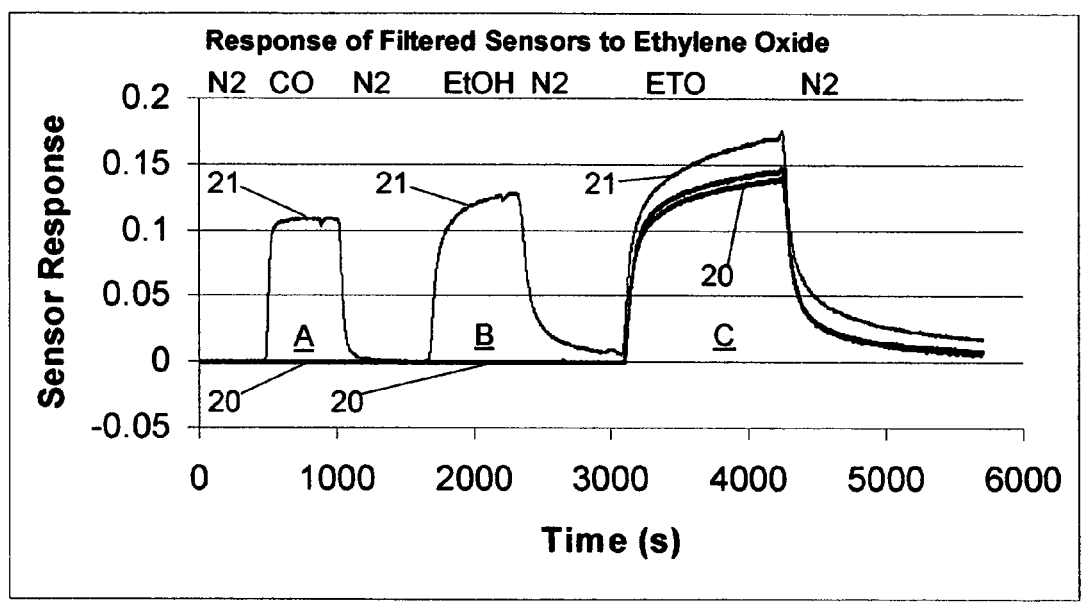
FIG. 2 Experimental data showing the response of an electrochemical based monitor to successive exposures to 10 ppm each carbon monoxide (CO), ethanol (EtOH) and ethylene oxide (ETO), with and without a filter.

FIG. 2 shows experimental data obtained using a filter as described above, employing silver (II) oxide as the filter medium. For the purposes of this invention, the term silver (II) oxide includes all chemical species with the approximate stoichiometric formula of AgO, including chemical species with silver in other oxidation states, such as a blend of silver (I) and silver (III) ions. In this experiment filters were placed in the gas path of two Chemdaq Corporation gas monitors immediately in front of the sensor, similar to the arrangement shown in FIG. 1; and a third monitor without a filter was used as control. The three test gases were carbon monoxide, ethanol and ethylene oxide all at 10 ppm in nitrogen, applied to the monitors at 500 ml/min or just nitrogen as a zero gas. The three monitors were connected to the same gas line, with the control situated last. At the start of the experiment (time=0), the monitors had nitrogen applied and as expected there was no response from any of the monitors. At approximately 500 seconds, carbon monoxide was applied and response curve A was produced from the control monitor 21, but the response from the filtered monitors 20 remained at the baseline. At approximate time of 1000 seconds, the carbon monoxide was turned off and nitrogen applied again and the control monitor response 21 returned to the baseline zero. At approximately 1600 seconds, ethanol was applied to all three monitors. The output from the control 21 rose to form response curve B, but the filtered monitors 20 remained at baseline. At approximately 2300 seconds the ethanol was turned off and nitrogen applied again and the signal from the control monitor 21 returned towards zero. At approximately 3100 seconds, ethylene oxide test gas was applied and all three monitors responded as is shown in response curve C. The unfiltered monitor 21 gas a slightly higher response than the filtered monitors 20, but this small difference between response curves 20 and 21 is readily accommodated by calibration. This experiment demonstrated the efficiency of the new filter. Using conventional electrochemical sensors, the filtered monitors 20 exhibited no detectable response to ethanol or carbon monoxide, but gave a strong response to ethylene oxide. Thus this filter has solved the primary drawback of the electrochemical sensors, i.e. their cross sensitivity to EOVCs including ethanol and carbon monoxide. Additional testing (not shown) demonstrated that this filter removes isopropanol (propan 2-ol) $CH_3CH(OH)CH_3$, at least as efficiently as it does ethanol.

I claim:

1. A method for the detection of ethylene oxide comprising:
   passing a gaseous sample through a filter,
      wherein the filter comprises an oxidizing agent, and
      wherein the filter is capable of oxidizing and reducing passage of an easily oxidizable volatile compound, and is substantially non-reactive with ethylene oxide; and
   allowing passage of ethylene oxide through the filter medium;
   passing the filtered gaseous medium to an ethylene oxide sensor; and
   monitoring the presence of ethylene oxide in the filtered gaseous medium.

2. The method of claim 1, wherein the oxidizing agent is selected from the group consisting of manganese dioxide, lead dioxide, silver (II) oxide and an oxide of vanadium.

3. The method of claim 1, wherein the sensor and the filter are disposed in a single housing.

4. The method of claim 1, wherein the sensor is disposed in a housing separate from the filter.

5. The method of claim 1, wherein the sensor is an electrochemical sensor.

6. The method of claim 1, wherein the easily oxidizable volatile compound comprises ethanol, isopropanol or carbon monoxide.

7. A method for the detection of ethylene oxide comprising:
   passing a gaseous medium through a filter, wherein the filter comprises silver (II) oxide,
      wherein said filter is capable of oxidizing and reducing passage of an easily oxidizable volatile compound, and is substantially non-reactive with ethylene oxide,
   passing the filtered gaseous medium to an ethylene oxide sensor, and
   monitoring the presence of ethylene oxide in the filtered gaseous medium.

8. The method of claim 7, wherein the sensor and the filter are disposed in a single housing.

9. The method of claim 7, wherein the sensor is disposed in a housing separate from the filter.

10. The method of claim 7, wherein the sensor is an electrochemical sensor.

11. The method of claim 7, wherein the filter is capable of removing one or more easily oxidizable volatile-compounds selected from the group consisting of ethanol, isopropanol, and carbon monoxide from the gaseous medium, thus preventing the easily oxidizable compound from reaching the ethylene oxide sensor.

12. The method of claim 7, wherein the passing occurs by diffusion.

13. A method for the detection of ethylene oxide comprising:
   passing a gaseous medium through a filter,
      wherein the filter comprises a polymeric organic compound,
      wherein the polymeric organic compound comprises a functional group selected from a group capable of passive hydrogen bonding, a basic group, and a strongly acidic group, and
      wherein the filter is capable of reducing passage of an alcohol and allowing passage of ethylene oxide;
   passing the filtered gaseous medium to an ethylene oxide sensor, and
   monitoring the presence of ethylene oxide in the filtered gaseous medium.

14. The method of claim 13, wherein the polymeric organic compound comprises a pyridine, a quaternary ammonium salt, an amine, an amine salt, a sulfonic acid or a mixture thereof.

15. The method of claim 13, wherein the sensor and the filter are disposed in a single housing.

16. The method of claim 13, wherein the sensor is disposed in a housing separate from the filter.

17. The method of claim 13, wherein the sensor is an electrochemical sensor.

18. The method of claim 13, wherein the alcohol is ethanol or isopropanol.

* * * * *